United States Patent [19]  [11] Patent Number: 4,843,168
Drezdzon et al.  [45] Date of Patent: Jun. 27, 1989

[54] CATALYSIS USING PILLARED HYDROTALCITES

[75] Inventors: Mark A. Drezdzon, Aurora; Eric J. Moore, Carol Stream; Mark P. Kaminsky, Lisle, all of Ill.

[73] Assignee: Amoco Corporation, Chicago, Ill.

[21] Appl. No.: 136,364

[22] Filed: Dec. 22, 1987

[51] Int. Cl.$^4$ .................... C07C 119/48; C07C 4/02; C07C 2/64

[52] U.S. Cl. .................... 558/357; 585/440; 585/443; 585/444

[58] Field of Search .............. 585/440, 443, 444; 558/357

[56] References Cited

U.S. PATENT DOCUMENTS

| | | | |
|---|---|---|---|
| 3,879,525 | 4/1975 | Miyata et al. | 423/277 |
| 4,033,767 | 7/1977 | Colegate et al. | 502/62 |
| 4,033,858 | 6/1977 | Granquist | 502/80 |
| 4,458,026 | 7/1984 | Reichle | 502/80 |
| 4,539,306 | 9/1985 | Chang | 502/154 |
| 4,629,713 | 12/1986 | Suzaki et al. | 502/62 |

Primary Examiner—Curtis R. Davis
Attorney, Agent, or Firm—Reed F. Riley; William H. Magidson; Ralph C. Medhurst

[57] ABSTRACT

Magnesium-aluminum, hydrotalcite-type clay compositions containing large, pillaring organic, inorganic, and mixed organic/inorganic anions have been made. Heating of the mixed large organic/inorganic anion hydrotalcite-type clays can lead to substantially complete removal of the organic anions and a route to making large, inorganic-anion, hydrotalcite-type clays with more open galleries. These materials are shown to catalyze hydrocarbon conversion reactions.

11 Claims, No Drawings

CATALYSIS USING PILLARED HYDROTALCITES

BACKGROUND OF THE INVENTION

This invention relates to catalyzed processes employing organic and inorganic anion-pillared clay compositions having the hydrotalcite crystal structure and, more particularly, to catalyzed processes employing anionic magnesium-aluminum hydrotalcite clays having large inorganic and/or organic anions located interstitially between positively charged layers of metal hydroxides and a method of preparation of such anion-pillared clays to form anionic clays where the anion is at least in part a polyoxometalate anion.

Clay minerals are composed of infinite layers of metal or nonmetal oxides and hydroxides stacked one on top of the other. In the case of the widely-found cationic clays, interlayer cations ($Na^+$, $Ca^{2+}$ etc.) charge neutralize the negatively charged oxide/hydroxide sheets. The far less common anionic clays have positively charged metal oxide/hydroxide layers with anions located interstitially. Many of these are based on double hydroxides of such main group metals as Mg, and Al and transition metals such as Ni, Co, Cr, Zn and Fe etc. These clays have a structure similar to brucite [$Mg(OH)_2$] in which the magnesium ions are octahedrally surrounded by hydroxyl groups with the resulting octahedra sharing edges to form infinite sheets. In the anionic clays, some of the magnesium is isomorphously replaced by a trivalent ion, say $Al^{3+}$. The $Mg^{2+}$, $Al^{3+}$, $OH^-$ layers are then positively charged necessitating charge balancing by insertion of anions between the layers. One such clay is hydrotalcite in which the carbonate ion is the interstitial anion. Rhobohedral hydrotalcite has the idealized unit cell formula [$Mg_6Al_2(OH)_{16}$]$CO_3.4H_2O$. However, the ratio of Mg/Al in hydrotalcite can vary between 1.7 and 4 and various other divalent and trivalent ions may be substituted for the magnesium and aluminum. In addition, the anion, which is carbonate in hydrotalcite, can be varied in synthesis by a large number of simple anions such as $NO_3^-$, $Cl^-$, $OH^-$, $SO_4^{2-}$ etc. Substitution techniques which have been used are ion exchange and acid treatment in the presence of the desired anion.

Processes for making hydrotalcite clay have been the subject of a number of patents. See, for example, U.S. Pat. Nos. 4,539,306, 4,539,195 and 3,539,306. These patents are largely directed to pharmaceutical uses for hydrotalcite. Miyata et al. in U.S. Pat. Nos. 3,796,792, 3,879,523, and 3,879,525 describes hydrotalcites with both cationic layer and anionic substitution including the transition metal anions $CrO_4^{2-}$, $MoO_4^{2-}$ and $Mo_2O_7^{2-}$. Both compositions and preparative methods are described, and the compositions are said to be useful for catalytic purposes, absorbents, dessicants and the like. In U.S. Pat. Nos. 4,458,026 and 4,476,324 and Journal of Catalysis 94, 547–557 (1985), Reichle describes synthetic hydrotalcites containing small anions, including anions of some transition elements, and also large organic anions such as long chain aliphatic alpha-omega dicarboxylates. However, no X-ray data is given to support his assumption that the carboxylate anion is in the lattice. Reichle has shown that the hydrotalcites can catalyze aldol condensations effectively. Miyata and Kumura in Chemistry Letters pp. 843–8 (1973) describe hydrotalcite clay materials containing $Zn^{2+}$ and $Al^{3+}$ with dicarboxylate anions and show that the interlayer spacing obtained using X-ray diffraction expands from 9.4 Angstroms to about 19 Angstroms as the dicarboxylate anion is changed along the series oxalate, malonate, succinate, adipate and sebacate. This study indicates the carboxylate anions are in the lattice standing roughly perpendicular to the layers.

The success of molecular sieves for catalytic purposes has prompted a search for other porous inorganic materials which could act as shape selective catalysts. Pillared cationic clays have been investigated as part of this search but the small number of useful large cations and the small amount of open volume left after completely pillaring some of the materials has been a concern. Also, the poor thermal stability of several of the cationic pillars has been discouraging since the pillars collapse during higher temperature catalytic use. Anionic clays have also been considered, as has been reviewed above, but the work has resulted in no examples of anionic clays with catalytic potential i.e., clays with a large interlayer spacing, an incompletely stuffed gallery, and supported by inorganic anionic pillars containing a transition metal ion. Now a useful technique has been found to produce large organic anion pillared Mg/Al hydrotalcites with large interlayer spacings which can be exchanged with large transition-metal-containing anions to form Mg/Al hydrotalcites containing those inorganic ions. Partial replacement with such large inorganic ions can produce structures in which some of the hydroxide layer charge is compensated by smaller anions increasing the gallery space available to molecules diffusing into the structure from the outside and the potential for catalytic action. These pillared materials have been found to be useful catalysts for the conversion of organic substances.

SUMMARY OF THE INVENTION

Described herein are a pillared, hydrotalcite-structure compositions comprising compounds of formula [$Mg_{2x}Al_2(OH)_{4x+4}$]$Y^{n-}_{2/n}.ZH_2O$ having an X-ray diffraction d(003) value substantially greater than the hydrotalcite value of about 8 Angstroms, wherein Y is a large organic anion selected from the group consisting of lauryl sulfate, p-toluenesulfonate, terephthalate, 2,5-dihydroxy-1,4-benzenedisulfonate, and 1,5-naphthalenedisulfonate, and wherein x runs between about 1.5 to about 2.5, n is 1 or 2, and Z runs between zero and about 3.

Also described herein are pillared, hydrotalcitestructure compositions comprising compounds of formula [$Mg_{2x}Al_2(OH)_{4x+4}$]$A^{n-}_{2/n}.ZH_2O$ having an X-ray diffraction d(003) value substantially greater than the hydrotalcite value of about 8 Angstroms, wherein A is an anionic polyoxometalate selected from the group consisting of polyoxometalates of vanadium, tungsten and molybdenum, and wherein x runs between about 1.5 and about 2.5, n is 6, and Z runs between about zero and about 3.

Still another aspect of the invention includes processes to make pillared compositions, and products resulting therefrom, comprising contacting a hydrotalcite-structure composition comprising a compound of formula [$Mg_{2x}Al_2(OH)_{4x+4}$]$Y^{n-}_{2/n}.ZH_2O$ having an X-ray diffraction d(003) value substantially greater than the hydrotalcite value of about 8 Angstroms, wherein Y is a large organic anion selected from the group consisting of p-toluenesulfonate, terephthalate, 2,5-dihydroxy-1,4-benzenedisulfonate, and 1,5-naphthalenedisulfonate, and wherein x runs between about 1.5 to about 2.5, n is 1 or 2, and Z runs between zero and about 3 with a solution containing a polyoxometalate selected from the group consisting of polyoxometalates of vanadium, tungsten, and molybdenum at a pH of between about 3 and about 6 and a temperature between about 20° C. and about 100° C. whereby at least some of said large organic anion is substituted by the anion of said polyoxometalate.

Yet another aspect of the invention involves heating a pillared composition of the hydrotalcite structure which contains both large inorganic and organic anions as defined above until substantially all the large organic anion has been removed from the pillared composition.

Most importantly, the various pillared hydrotalcitetype clays taught herein are shown to be useful for catalytically converting organic substances.

DETAILED DESCRIPTION OF THE INVENTION

To make the organic, anion-pillared, hydrotalcitetype clays of this invention, a magnesium salt, an aluminum salt and the organic material intended as the interlayer species are combined in aqueous solutions. Any soluble salt of magnesium and aluminum such as the nitrate, sulfate, halide, etc., may be used, although the nitrate is preferred. The organic anion producing substance can be used in either its salt form, an alkali metal salt such as the sodium salt is preferred, or its acid form. If the acid form is used, it is made up in a solution containing a base, say sodium hydroxide, to give a solution of pH between about 10 and about 14, more preferably between about 11 and about 13. Useful organic compounds such as dodecylsulfonic acid, p-toluenesulfonic acid, terephthalic acid, 2,5-dihydroxy-1,4-benzenedisulfonic acid, and 1,5-naphthalenedisulfonic acid and their mono-and di-alkali metal salts are useful. It is preferred to use terephthalic acid. Molar ratios of magnesium compound to aluminum compound preferred are about 1.5 to about 2.5, more preferably about 1.8 to about 2.2, and, most preferably about 2. The mols of organic material used per mol of $Mg^{2+}$ and $Al^{3+}$ compound depends upon the charge on the organic anion incorporated and the amount of the anionic clay to be made recognizing that each aluminum ion incorporated in the structure requires an extra negative charge in the interstitial layer.

The magnesium and aluminum salts are optimally mixed together and added slowly with stirring to a warmed solution of the organic anion-producing material in its acid form or salt form made by neutralizing the acid form using, e.g., sodium hydroxide. Whether the acid or salt form is used, the solution into which the Mg and Al salts are dripped should have a pH of about 10 to about 14, and, more preferably, about 11 to about 13. Slower addition and a more elevated temperature (an autoclave may be used) tends to produce larger crystals as may be understood by one skilled in the art. Because the carbonate ion is strongly preferred as the interlayer ion, exposure during preparation of the clay to carbon dioxide or carbonate ion is to be avoided.

In general, the organic anion pillared clays produced have the idealized formula $[Mg_{2x}Al_2(OH)_{4x+4}]Y^{n-}{}_{2/n} \cdot ZH_2O$, where Y is the large organic ion, x runs from about 1.5 to about 2.5, more preferably about 2, n is 1 or 2 and Z runs between zero and about 3. They are generally white, microcrystalline solids.

A study of the X-ray diffraction data shown in the Table below indicates that the large organic anions incorporated into the hydrotalcite-type materials shown are in the lattice in a more or less upright and extended position.

TABLE 1

| Anion Name | Anion Size[1] Å | d(003) Spacing Expected[2] Å | Observed[3] Å |
|---|---|---|---|
| terephthalate | 9.50 | 14.40 | 14.26 |
| 2,5-dihydroxy-1,4-benzenedisulfonate | 10.30 | 15.20 | 14.68 |
| p-toluenesulfonate | 9.90 | 14.80 | 17.18 |
| 1,5-naphthalenedisulfonate | 10.40 | 15.30 | 15.12 |
| dodecylsulfonate | 21.30 | 26.20 | 26.29 |

[1]Assumes the anion is oriented between the brucite layers for maximum pillar height.
[2]Expected d(003) spacing equals anion size plus brucite layer thickness (4.90 A).
[3]Average of several preparations in which the Mg/Al molar ratio is 2:1.

To make the completely exchanged, large-inorganic-anion, pillared hydrotalcite-type clays of this invention, an aqueous slurry of an organic anion-pillared hydrotalcite-type clay made from one of the pillaring organic anions listed above is acidified with an acid such as nitric, sulfuric, acetic and the like to a pH of about 3 to about 6, more preferably about 4 to about 5, and a compound on which the pillaring metalate anion is based is added. Preferably, the hydrotalcite-type clay is pillared by the terephthalate anion.

Preferably, a stoichiometric excess of the anion pillaring material over the hydrotalcite-type clay is used, for example, about a 1 to about 3 molar excess. The pillaring polyoxometalate anion is preferably a polyoxometalate of molybdenum, tungsten or vanadium. Since the composition of the polyoxometalate is pH dependent, the pH will determine the predominant polyoxometalate anion species present in solution and possibly in the hydrotalcite-type clay formed by exchanging out the organic anion pillar. More preferably, the anionic polyoxometalate pillar is an anion selected from the group consisting of $(Mo_7O_{24})^{-6}$, $(W_7O_{24})^{6-}$ and $(V_{10}O_{28})^{6-}$. Most preferably, the anionic polyoxometalate pillar is the $(Mo_7O_{24})^{6-}$ ion. It is definitely preferred to use an aqueous slurry of the organic-anion-pillared hydrotalcite-type clay fresh from its preparation. If the organic-anion-pillared clay is dried after preparation and then slurried it has been found to be far less reactive and the exchange of the inorganic pillars for the organic pillars proceeds far less completely and more slowly.

In general, the inorganic anion-pillared clays have the idealized formula $[Mg_{2x}Al_2(OH)_{4x+4}]A^{n-}{}_{2/n} \cdot ZH_2O$, where A is the polyoxometalate anion, x runs from about 1.5 to about 2.5, more preferably about 2, n is 6, and Z runs between zero and about 3.

The X-ray diffraction data shown in the Table below indicates the anions of the molybdenum, tungsten and vanadium-pillared, hydrotalcite-type clays are present in the lattice in the most energetically favorable orientation. However, this is not necessarily the case for each anion pillar that could be used.

TABLE 2

| Anion Formula | d(003) Spacing (Å) Least Energy* Orientation | Higher Energy* Orientation | Observed Value |
|---|---|---|---|
| $(Mo_7O_{24})^{6-}$ | 12.1 | 15.24, 16.46 | 12.2 |
| $(W_7O_{24})^{6-}$ | 12.1 | 15.24, 16.46 | 12.1 |
| $(V_{10}O_{26})^{6-}$ | 11.95 | 12.98, 15.26, 15.99 | 12.3 |

*Calculated from literature values assuming Van der Waals contact between anions and brucite layers.

By changing exchange conditions such as adding less than the amount of polyoxometalate anion necessary to completely remove all the organic anion pillars, a mixed organic/inorganic pillared hydrotalcite can be formed. Otherwise, the conditions are similar to those used to completely exchange the organic anion pillars by inorganic anion pillars. Preferably, the terephthalate-pillared, hydrotalcite-type clay is used for partial exchange.

In general, the mixed inorganic-organic anion-pillared clays have the idealized formula $[Mg_{2x}Al_2(OH)_{4x+4}](Y^{n-}-A^{m-})_{2/n+m} \cdot ZH_2O$, where x runs between about 1.5 to about 2.5, more preferably about 2, Y is the organic anion pillar, n is 1 or 2, A is the inorganic anion pillar, m is 6, and Z runs between zero and about 3.

The interlayer spacing, d(003), of these mixed organic/inorganic anion pillared materials changes from a value typical of the organic anion pillared species to a value typical of the inorganic anion pillared material as the organic anion is replaced.

It has been found that the organic anion pillars of a mixed organic/inorganic anion pillared clay can be substantially completely removed by, for example, heating. Calcining temperature depends upon the length of the heating time to some extent, but heating at above 400° to 500° C. usually effects substantial removal. Care should be taken not to heat the clay at too high a temperature or the framework structure will collapse.

The anionic hydrotalcite clays of this invention are found to be useful for such diverse purposes as dessicants, absorbents and as basic catalysts.

The hydrotalcite-type, anionic-pillared or partially pillared clays of the instant invention can be used as stated above for heterogeneously-catalyzed organic compound conversion. They have been shown, for example, to effectively catalyze the vapor phase dehydrogenation or ammoxidation of hydrocarbons, in particular, alkyl aromatic hydrocarbons. The dehydrogenations can be either thermal or oxidative. For example, such materials as a lower alkyl ethylbenzene or propylbenzene may be dehydrogenated to a substituted styrene or cymene. And a xylene may be selectively converted to a dicyanobenzene by ammoxidation using oxygen and ammonia.

In carrying out a vapor phase dehydrogenation using these inorganic anion, hydrotalcite-type pillared clays, the process temperature generally runs between about 200° C. and about 600° C., more preferably, between about 300° C. and about 500° C. Total pressures useful in the process can be anywhere between about 0.1 atm and several hundred atms, but a pressure of about 1 to about 300 atms is preferred. Weight-hourly space velocities useful in these catalyzed dehydrogenations are in the range of about 0.1 to about 20 $hrs.^{-1}$, more preferably, about 0.5 to about 5 $hrs.^{-1}$. oxygen is used in the dehydrogenation, the oxygen-hydrocarbon feed molar ratios can be varied over a substantial range as can be understood by one skilled in the art.

Such hydrocarbons as a $C_1$ to $C_5$ lower alkyl substituted ethylbenzene can be employed. More preferably, p-(methyl) or p-(t-butyl)ethylbenzene is dehydrogenated by using these pillared clays.

In carrying out heterogeneously catalyzed, vapor phase ammoxidations over these inorganic anion, hydrotalcite-type pillared clays, the process feed is a mixture of a hydrocarbon which can be, for example, a lower alkyl mono or di-substituted benzene or naphthalene, oxygen, optionally in an inert diluent like nitrogen, and ammonia. The reaction temperature used is customarily between about 200° C. and about 600° C., and reaction total pressure is usefully about 1 atm to several hundred atms. Space velocities useful in these ammoxidations are in the range of from about 0.1 to about 20 $hrs.^{-1}$, more preferably, about 0.2 to about 5 $hrs.^{-1}$. Molar ratios of hydrocarbon, oxygen, and ammonia in the feed can be varied over a wide range of values as may be understood by one skilled in the art.

The pillared clays of this invention can be used either supported by an inorganic support as silica, alumina, silica-alumina, etc., or unsupported. Preferably, they are used unsupported. Catalyst particle size will depend upon whether or not the pillared is supported and whether a fixed bed or ebullated bed reactor is employed.

The following Examples will serve to certain embodiments of the herein disclosed invention. These Examples should not, however, be construed as limiting the scope of the novel invention as there are many variations which may be made thereon without departing from the spirit of the disclosed invention, as those of skill in the art will recognize.

EXAMPLE

General

Analytical data (Na, Mg, Al) was obtained either by the atomic absorption or inductively coupled plasma technique. Carbonate analysis was done volumetrically by $CO_2$ evolution and C and H by a high accuracy C, H analysis. Powder XRD was used to check crystallinity and determine the d(003) spacing (layer spacing). Where crystallinity was insufficient or interlayer spacing too large to determine the d(003) spacing accurately, it was determined by preferred orientation XRD, PO-XRD. Surface areas were measured using nitrogen by the BET procedure. Scanning electron microscopy (SEM) was used to determine the homogeneity of certain pillared products.

COMPARATIVE EXAMPLE 1

A 3 l, 3-necked round bottom flask equipped with a thermometer, reflux condenser, and mechanical stirrer was charged with 1200 ml of deionized water, 64.3 g of $Na_2CO_3$, and 340.6 g of 50% NaOH solution. A second solution containing 308.3 g of $Mg(NO_3)_2 \cdot 6H_2O$, 225.0 g of $Al(NO_3)_3 \cdot 9H_2O$, and 960 ml of deionized water was prepared and added dropwise to the first solution with stirring over a period of 75 mins. After addition was complete, the gel-like mixture was heated for 16 hrs at 64°-86° C. The cooled mixture was then filtered, yielding a white, wet filter cake. The latter was reslurried in 750 ml of deionized water and filtered, a technique which was repeated twice. The resulting product was dried overnight at 125°-130° C. in a vacuum oven giving a hard, white solid. The Mg/Al atomic ratio of the product was 2.19. The carbonate content was 12.39 wt. %, corresponding to a $CO_3/Al$ molar ratio of 0.51. The powder XRD pattern was indexed to hydrotalcite and the d(003) spacing found to be 7.78 Å. The surface area of the solid was 62 sq m/g. The physical properties of the material show it to be synthetic hydrotalcite, $[Mg_6Al_2(OH)_{16}]CO_3 \cdot 4H_2O$.

EXAMPLE 2

A 5 l, 3-necked round bottom flask equipped with a thermometer, reflux condenser, and mechanical stirrer was charged with 1600 ml of deionized water, 133.06 g of terephthalic acid, and 576.56 g of 50% NaOH solution. A second solution containing 410.40 g of $Mg(NO_3)_2.6H_2O$. 300.0 g of $Al(NO_3)_3.9H_2O$, and 1280 ml of deionized water was prepared and added dropwise to the first solution with stirring over a period of 60 mins. After addition was complete, the gel-like mixture was heated for 18 hrs at 73°–75° C. The cooled mixture was then filtered, yielding a white, wet filter cake. The latter was reslurried in 2 l of deionized water and filtered, a technique which was repeated twice. The thus washed material was reslurried with 2 l of deionized water and stored for further use. The Mg/Al atomic ratio of the product was 2.30. The carbon content was 9.23 wt. %, corresponding to a terephthalate/Al molar ratio of 0.34. The d(003) spacing was found to be 14.5 Å. by PO-XRD. The material was homogeneous by SEM. The wt. % clay in the final aqueous slurry was 7.59%.

EXAMPLE 3

A 5 l, 3-necked round bottom flask equipped with a thermometer, reflux condenser, and mechanical stirrer was charged with 1600 ml of deionized water, 304.4 g of paratoluene sulfonic acid monohydrate, and 576.0 g of 50% NaOH solution. A second solution containing 410.2 g of $Mg(NO_3)_2.6H_2O$, 300.08 g of $Al(NO_3)_3.9H_2O$, and 1280 ml of deionized water was prepared and added dropwise to the first solution with stirring over a period of 65 mins. After addition was complete, the gel-like mixture was heated for 20 hrs at 69°–81° C. The cooled mixture was then filtered, yielding a white, wet filter cake. The latter was reslurried in 2 l of deionized water and filtered, a technique which was repeated twice. The thus washed material was reslurried with 2 l of deionized water and stored for further use. The Mg/Al atomic ratio of the product was 2.39. The carbon content was 23.86 wt. %, corresponding to a paratoluenesulfonate/Al molar ratio of 1.00. The d(003) spacing was found to be 17.1 Å by PO-XRD. The wt. % clay in the final aqueous slurry was 4.78%.

EXAMPLE 4

A 3 l, 4-necked round bottom flask equipped with a thermometer, reflux condenser, mechanical stirrer, and nitrogen inlet tube was charged with 960 ml of deionized water. After bubbling the water with nitrogen for 20 mins, 134.4 g of NaOH pellets and 159.5 g of disodium 1,5-naphthalenedisulfonate were added to the water. A second solution containing 246.1 g of $Mg(NO_3)_2.6H_2O$, 180.0 g of $Al(NO_3)_3.9H_2O$, and 768 ml of deionized water was prepared and added dropwise to the first solution with stirring over a period of 50 mins. After addition was complete, the gel-like mixture was heated for 18 hrs at 75°–78° C. under a slow nitrogen purge. The cooled mixture was then filtered, yielding a white, wet filter cake. The latter was reslurried in 2 l of deionized water and filtered, a technique which was repeated twice. The thus washed material was reslurried with 2 l of deionized water and stored for further use. The Mg/Al atomic ratio of the product was 2.38. The carbon content was 12.96 wt. %, corresponding to a 1,5-naphthalenedisulfonate/Al molar ratio of 0.42. The d(003) spacing was found to be 15.3 Å by PO-XRD. The wt. % clay in the final aqueous slurry was 3.71%.

EXAMPLE 5

A 5 l, 3-necked round bottom flask equipped with a thermometer, reflux condenser, and mechanical stirrer was charged with 1000 ml of deionized water, 288 g of sodium lauryl sulfate, and 279.8 g of 50% NaOH solution. A second solution containing 256.5 g of $Mg(NO_3)_2.6H_2O$, 187.5 g of $Al(NO_3)_3.9H_2O$, and 800 ml of deionized water was prepared and added dropwise to the first solution with stirring over a period of 70 mins. After addition was complete, the foamy, viscous mixture was heated for 19 hrs at 75°–80° C. The cooled mixture was filtered, yielding a white paste-like filter cake. The latter was reslurried in 2 l of deionized water and filtered, a technique which was repeated twice. The thus washed material was reslurried with 2 l of deionized water and stored for further use. The Mg/Al atomic ratio of the product was 2.60. The carbon content was 28.53 wt. %, corresponding to a lauryl sulfate/Al molar ratio of 1.40. The d(003) spacing was found to be 26.3 Å by PO-XRD. The wt. % clay in the final aqueous slurry was 5.75%.

EXAMPLE 6

A 5 l, 3-necked round bottom flask equipped with a thermometer, reflux condenser, and mechanical stirrer was charged with 1600 ml of deionized water, 449.0 g of 50% NaOH solution, and 227.0 g of dipotassium 2,5-dihydroxy-1,4-benzenedisulfonate. A second solution containing 410.14 g of $Mg(NO_3)_2.6H_2O$, 300.0 g of $AL(NO_3)_3.9H_2O$, and 1280 ml of deionized water was prepared and added dropwise to the first solution with stirring over a period of 75 mins. After addition was complete, the gel-like mixture was heated for 18 hrs at 73°–79° C. The cooled mixture was then filtered, yielding a yellowish, wet filter cake. The latter was reslurried in 2 l of deionized water and filtered, a technique which was repeated twice. The thus washed material was reslurried with 2 l of deionized water and stored for further use. The Mg/Al atomic ratio of the product was 1.94. The carbon content was 9.56 wt. %, corresponding to a 2,5-dihydroxy-1,4-benzenedisulfonate/Al molar ratio of 0.56. The d(003) spacing was found to be 14.7 Å by PO-XRD. The wt. % clay in the final aqueous slurry was 7.1%.

COMPARATIVE EXAMPLE 7

A 5 l, 3-necked round bottom flask equipped with a thermometer, reflux condenser, and mechanical stirrer was charged with 2000 ml of deionized water, 162.1 g of disodium succinate, and 558.8 g of 50% NaOH solution. A second solution containing 513.6 g of $Mg(NO_3)_2.6H_2O$, 375.3 g of $Al(NO_3)_3.9H_2O$, and 1600 ml of deionized water was prepared and added dropwise to the first solution with stirring over a period of 135 mins. After addition was complete, the gel-like mixture was heated for 18 hrs at 68°–76° C. The cooled mixture was then filtered, yielding a white, wet filter cake. The latter was reslurried with 2 l of deionized water and filtered, a technique which was repeated twice. The thus washed material was reslurried with 2 l of deionized water and stored for further use. The Mg/Al atomic ratio of the product was 2.45. The carbon content was 1.84 wt. %, corresponding to a succinate/Al molar ratio of 0.11. The d(003) spacing was found to be 7.85 Å by powder XRD, indicating that the structure is not pillared by succinate anions standing perpendicular to the clay sheets.

COMPARATIVE EXAMPLE 8

A 5 l, 3-necked round bottom flask equipped with a thermometer, reflux condenser, and mechanical stirrer was charged with 2000 ml of deionized water, 201.75 g of sebacic acid, and 719.3 g of 50% NaOH solution. A second solution containing 513.8 g of $Mg(NO_3)_2.6H_2O$, 376.0 g of $Al(NO_3)_3.9H_2O$, and 1600 ml of deionized water was prepared and added dropwise to the first solution with stirring over a period of 120 mins. After addition was complete, the gel-like mixture was heated for 16 hrs at 61°–71° C. The cooled mixture was then filtered, yielding a white, wet filter cake. The latter was reslurried with 2 l of deionized water and filtered, a technique which was repeated twice. The thus washed material was reslurried with 2 l of deionized water and stored for further use. The Mg/Al atomic ratio of the product was 2.58. The carbon content was 4.22 wt. %, corresponding to a sebacate/Al molar ratio of 0.10. The d(003) spacing was found to be 7.91 Å by powder XRD, indicating that the structure is not pillared by sebacate anions standing perpendicular to the clay sheets.

COMPARATIVE EXAMPLE 9

A 3 l, 3-necked round bottom flask equipped with a thermometer, reflux condenser, and mechanical stirrer was charged with 960 ml of deionized water, 97.08 g of sebacic acid, and 499.2 g of 50% NaOH solution. A second solution containing 492.3 g of $Mg(NO_3)_2.6H_2O$, 180.2 g of $Al(NO_3)_3.9H_2O$, and 768 ml of deionized water was prepared and added dropwise to the first solution with stirring over a period of 60 mins. After addition was complete, the gel-like mixture was heated for 19 hrs at 75°–83° C. The cooled mixture was then filtered, yielding a white, wet filter cake. The latter was reslurried with 2 l of deionized water and filtered, a technique which was repeated twice. The thus washed material was reslurried with 2 l of deionized water and stored for further use. The Mg/Al atomic ratio of the product was 4.02. The carbon content was 1.25 wt. %, corresponding to a sebacate/Al molar ratio of 0.04. The d(003) spacing was found to be 7.97 Å by powder XRD, indicating that the structure is not pillared by sebacate anions standing perpendicular to the clay sheets.

COMPARATIVE EXAMPLE 10

A 3 l, 4-necked round bottom flask equipped with a thermometer, reflux condenser, mechanical stirrer, and nitrogen inlet tube was charged with 1100 ml of deionized water. After bubbling the water with nitrogen for 10 mins, 70.1 g of adipic acid and 172.0 g of NaOH pellets were added to the water. A second solution containing 246.1 g of $Mg(NO_3)_2.6H_2O$, 180.2 g of $Al(NO_3)_3.9H_2O$, and 768 ml of deionized water was prepared and added dropwise to the first solution with stirring over a period of 45 mins. After addition was complete, the gel-like mixture was heated for 18 hrs at 74°–84° C. under a slow nitrogen purge. The cooled mixture was then filtered, yielding a white, wet filter cake. The latter was reslurried in 2 l of deionized water and filtered, a technique which was repeated twice. The thus washed material was reslurried with 2 l of deionized water and stored for further use. The Mg/Al atomic ratio of the product was 2.45. The carbon content was 3.40 wt. %, corresponding to a adipate/Al molar ratio of 0.13. The d(003) spacing was found to be 7.79 Å by powder XRD, indicating that the structure is not pillared by adipate anions standing perpendicular to the clay sheets.

COMPARATIVE EXAMPLE 11

A 3 l, 4-necked round bottom flask equipped with a thermometer, reflux condenser, mechanical stirrer, and nitrogen inlet tube was charged with 960 ml of deionized water. After bubbling the water with nitrogen for 20 mins, 70.15 g of adipic acid and 211.2 g of NaOH pellets were added to the water. A second solution containing 428.4 g of $Zn(NO_3)_2.6H_2O$, 180.6 g of $Al(NO_3)_3.9H_2O$, and 768 ml of deionized water was prepared and added dropwise to the first solution with stirring over a period of 50 mins. After addition was complete, the gel-like mixture was heated for 16 hrs at 79°–80° C. under a slow nitrogen purge. The cooled mixture was then filtered, yielding a white, wet filter cake. The latter was reslurried in 2 l of deionized water and filtered, a technique which was repeated twice. The thus washed material was reslurried with 2 l of deionized water and stored for further use. The Zn/Al atomic ratio of the product was 3.24. The carbon content was 0.62 wt. %, corresponding to a adipate/Al molar ratio of 0.06. The d(003) spacing was found to be 7.67 Å by PO-XRD, indicating that the structure is not pillared by adipate anions standing perpendicular to the clay sheets.

EXAMPLE 12

To a 2654 g portion of a 7.59 wt. % slurry of the terephthalate-pillared hydrotalcite of Example 2 was added a solution containing 240.08 g of $Na_2MoO_4.2H_2O$ in 800 ml of deionized water. After stirring the mixture for about 15 mins, the mixture was aidified to a pH of 4.4 with 2N $HNO_3$. After stirring for 5 mins, the mixture was filtered, affording a pale yellow, wet filter cake. The latter was reslurried with 2 l of deionized water and filtered, a technique which was repeated twice. The thus washed material was dried in a vacuum oven overnight at 125°–130° C. The Mg/Al atomic ratio of the product was 2.00. The Mo content of the product was 28.95 wt. %, corresponding to a Mo/Al atomic ratio of 1.18. The d(003) spacing was found to be 12.2 Å by PO-XRD. The material was homogeneous by SEM.

EXAMPLE 13

To a 1413 g portion of a 5.25 wt. % slurry of a terephthalate-pillared hydrotalcite was added a solution containing 73.91 g of $NaVO_3$ in 500 ml of deionized water. After stirring the mixture for about 15 mins, the mixture was acidified to a pH of 4.5 with 2N $HNO_3$. After stirring for 5 mins, the mixture was filtered, yielding a yellow-gold, wet filter cake. The latter was reslurried with deionized water and filtered, a technique which was repeated twice. The thus washed material was dried in a vacuum oven overnight at 125°–130° C. The Mg/Al atomic ratio of the product was 2.14. The V content of the product was 23.8 wt. %, corresponding to a V/Al atomic ratio of 1.67. The d(003) spacing was found to be 12.3 Å by PO-XRD. The material was homogeneous by SEM.

EXAMPLE 14

A 2800 g portion of a 4.73 wt. % slurry of a terephthalate-pillared hydrotalcite was split into a 1325 g and a 1475 g portion. To the 1325 g portion was added a solution containing 279.65 g of $Na_2WO_4.2H_2O$ in 600 ml of deionized water; to the 1475 g portion was added a solution containing 311.56 g of $Na_2WO_4.2H_2O$ in 650 ml of deionized water. Both mixtures were stirred for about 5 mins then acidified to a pH of 4.5 with 2N $HNO_3$. After stirring for 5 mins, the mixtures were filtered through the same apparatus, yielding a white, wet filter cake The latter was reslurried in 1 l of deionized water and filtered, a technique which was repeated twice. The thus washed material was dried in a vacuum oven overnight at 125°–130° C. The Mg/Al atomic ratio of the production was 1.92. The W content of the product was 42 wt. %, corresponding to a W/Al atomic ratio of 1.16. The d(003) spacing was found to be 12.1 Å by PO-XRD. The material was homogeneous by SEM.

EXAMPLE 15

To a 1233 g portion of a 7.73 wt. % slurry of a terephthalate-pillared hydrotalcite was added a solution containing 53.43 g of $Na_2MoO_4.2H_2O$ in 200 ml of deionized water. After stirring the mixture for about 5 mins, the mixture was acidified to a pH of 4.3 with 4N $HNO_3$. After stirring for 5 mins, the mixture was filtered, yielding a cream colored, wet filter cake. The latter was reslurried with deionized water and filtered, a technique which was repeated twice. The thus washed material was dried in a vacuum oven overnight at 125°–130° C. The Mg/Al atomic ratio of the product was 1.66. The Mo content of the product was 22.55 wt. %, corresponding to a Mo/Al atomic ratio of 0.80 (68% exchange) The d(003) spacings were found to be 12.2 Å and 14.4 Å by PO-XRD. The material was homogeneous by SEM and displayed a homogeneous elemental distribution by AEM. The surface area of the material was 26 sq m/g.

EXAMPLE 16

To a 1330 g portion of a 7.74 wt. % slurry of a terephthalate-pillared hydrotalcite was added a solution containing 24.50 g of $NaVO_3$ in 100 ml of deionized water. After stirring the mixture for about 20 mins, the mixture was acidified to a pH of 4.4 with 4N $HNO_3$. After stirring for 5 mins, the mixture was filtered, yielding a pale yellow, wet filter cake. The latter was reslurried with 2 l of deionized water and filtered, a technique which was repeated twice. The thus washed material was dried in a vacuum oven overnight at 125°–130° C. The Mg/Al atomic ratio of the product was 1.92. The V content of the product was 10.8 wt. %, corresponding to a V/Al atomic ratio of 0.64 (39% exchange). The d(003) spacing was found to be 14.3 Å by PO-XRD. The material was homogeneous by SEM and displayed a homogeneous elemental distribution by AEM. The surface area of the dried material was 40 sq m/g.

EXAMPLE 17

A portion of the partially-exchanged, molybdenum-pillared material of Example 15 was heated at 500° C. for 12 hrs. The resulting solid was found to be amorphous by XRD and homogeneous by SEM. Carbon analysis of the calcined product showed that the carbon content had decreased from 9.91% to 1.16%. The Mg/Al and Mo/Al ratios were found to be unchanged, and the surface area measured about the same as the starting material from Example 15.

EXAMPLE 18

A portion of the partially-exchanged, vanadium-pillared material of Example 16 was heated at 500° C. for 12 hrs. The product was found to be amorphous by XRD and homogeneous by SEM. Carbon analysis of the calcined product show that the carbon content had decreased from 7.12% to 0.41%. The Mg/Al and Mo/Al molar ratios were unchanged after heating. Calcining caused the mesopore volume of the product to increase from 0.11 cc/g to 0.19 cc/g and the surface area to increase from 40 to 123 sq m/g.

EXAMPLE 19

About 25 ml of a molybdate-pillared hydrotalcite was packed into a quartz reaction vessel. An 8% oxygen-in-nitrogen gas mixture was used with a gas mixture/p-(tbutyl)ethylbenzene molar diluent ratio of 14. The reaction was conducted at 500° C. and 1 atm total pressure with a WHSV of 0.15. Analysis of the products by gas chromatography revealed 54% conversion of the p-(tbutyl)ethylbenzene with 85% selectivity to p-(t-butyl) styrene. Dehydrogenation using a tungstate-pillared hydrotalcite and the same conditions gave 21% conversion and 57% selectivity.

EXAMPLE 20

About 2.8 ml of a vanadate-pillared hydrotalcite (18/40 mesh) was packed into a 0.9×26 cm quartz tube with a 1 cm long plug of α-alumina (18/40 mesh) and quartz wool on each end of the catalyst bed. The packed tube was heated to the desired reaction temperature using a small electric tube furnace. Eight percent oxygen in nitrogen and ammonia were fed to the reactor, and the flow rates were controlled electronically. The meta-xylene feed was metered into the reactor using a syringe pump.

The reaction of meta-xylene (0.0046 ml/min), dilute oxygen (60 ml/min), and ammonia (6.0 ml/min) was run for 2.5 hrs at 425° C. and 1 atm total pressure with the products produced subsequently condensed in a −77° C. cooled trap. The product was dissolved in THF, analyzed by gas chromatography, and found to be of the following composition:

| | |
|---|---|
| benzene | 0.69 area % |
| meta-xylene | 21.06 area % |
| benzonitrile | 14.94 area % |
| tolunitrile | 8.07 area % |
| dicyanobenzene | 54.30 area % |
| unidentified | 0.42 area % |

EXAMPLE 21

A 3 ml portion of 18/40 mesh molybdate pillared clay catalyst was mixed with 1 ml of 18/40 mesh alumina. The mixture was packed in a quartz tube in a similar fashion as Example 20. The catalyst was pretreated by heating under a 28 ml/min $N_2$ flow at 300° C. for 1 hr. An electronic flow controller was used to control the $N_2$ flow. Liquid p-cymeme was metered into the reactor using a syringe pump.

The reaction was run both oxidatively (8% $O_2$ in $N_2$) and nonoxidatively. Higher conversions and selectivities were observed under nonoxidative conditions. Under the conditions of 1 atm pressure, 580° C. reaction temperature, 0.0176 ml/min p-cymeme flow rate, 28 ml/min $N_2$ flow rate, and 6 hours on stream the products, as analyzed by gas chromatography, were found to have the following composition:

| Product | G.C. area % |
| --- | --- |
| toluene | 2.1 |
| para-cymene | 31.2 |
| para-methyl-alpha-methyl-styrene | 58.7 |
| unidentified | 7.3 |

What is claimed is:

1. A process to dehydrogenate a $C_1$ to $C_5$ alkyl-substituted ethyl benezene to a $C_1$ to $C_5$ alkyl-substituted styrene comprising contacting said alkyl-substituted ethylbenzene under dehydrogenation conditions with a catalyst comprising a pillared, hydrotalcite-structure composition of formula $[Mg_{2x}Al_2(OH)_{4x+4}]A^{n-}{}_{2/n} \cdot ZH_2O$ having an X-ray diffraction d(003) value substantially greater than the hydrotalcite value of about 8 Angstroms, wherein A is an anionic polyoxometalate selected from the group consisting of polyoxometalates of vanadium, tungsten, and molybdenum, and x runs between about 1.5 and about 1.5, n is 6, and Z runs between about 0 to 3.

2. The process of claim 1 wherein x is about 2 and $A^{n-}$ is $(Mo_7O_{24})^{6-}$ or $(V_{10}O_{28})^{6-}$.

3. The process of claim 2 wherein said $C_1$ to $C_5$ alkyl-substituted ethyl benzene is t-butylethylbenzene.

4. The process of claim 2 wherein said $C_1$ to $C_5$ alkyl-substituted ethyl benzene is p-methylethylbenzene or p-(t-butyl)ethylbenzene.

5. The process of claim 1 wherein x is about 2 and $A^{n-}$ is $(Mo_7O_{24})^{6-}$.

6. The process of claim 5 wherein said $C_1$ to $C_5$ alkyl-substituted ethyl benzene is p-cymene.

7. A process to ammoxidize a methyl-substituted benzene comprising contacting said methyl-substituted benzene under ammoxidation conditions with a catalyst comprising a pillared, hydrotalcite-structure composition of formula $[Mg_{2x}Al_2(OH)_{4x+4}]A^{n-}{}_{2/n} \cdot ZH_2O$ having an X-ray diffraction d(003) value substantially greater than the hydrotalcite value of about 8 Angstroms, wherein A is an anionic polyoxometalate selected from the group consisting of polyoxometalates of vanadium, tungsten, and molybdenum, and x runs between about 1.5 and about 2.5, n is 6, and Z runs between about zero and about 3.

8. The process of claim 7 wherein x is about 2 and $A^{n-}$ is $(V_{10}O_{28})^{6-}$.

9. The process of claim 8 wherein said methyl-substituted benzene is a xylene.

10. A process to convert an organic material comprising contacting said material under conversion conditions with a catalyst comprising a pillared, hydrotalcite-structure composition made by calcining a compound of formula $[Mg_{2x}Al_2(OH)_{4x+4}](Y^{n-}A^{m-})_{2/n+m} \cdot ZH_2O$, where x runs between about 1.5 to about 2.5, Y is an organic anion pillar, n is 1 or 2, A is an inorganic anion pillar, m is 6, and z runs between zero and about 3 until substantially all said organic anion pillar is removed 11. The process of claim 10 wherein said calcining is done at about 500° C.

* * * * *

UNITED STATES PATENT OFFICE
CERTIFICATE OF CORRECTION

Patent No. 4,843,168          Dated June 27, 1989

Inventor(s) MARK A. DREZDZON, ERIC J. MOORE and MARK A. KAMINSKY

It is certified that error appears in the above-identified patent and that said Letters Patent is hereby corrected as shown below:

Col. 2, line 47, delete "hydrotalcitestructure" and insert --hydrotalcite-structure--.

Col. 3, lines 14-15, delete "hydrotalcitetype" and insert --hydrotalcite-type--.

Col. 3, line 20, delete "hydrotalcitetype" and insert --hydrotalcite-type--.

Col. 5, line 56, delete "oxygen" and insert --If oxygen--.

Col. 6, line 12, before "as" add --such--.

Col. 6, line 18, after "will serve to" add --illustrate--.

Col. 8, line 23, change "A" to --$\text{Å}$--.

Col. 8, line 44, Change "A" to --$\text{Å}$--.

Col. 10, line 35, delete "aidified" and insert --acidified--.

Col. 11, line 12, delete "production" and insert --product--.

Col. 13, line 14, delete "benezene" and insert --benzene--.

UNITED STATES PATENT OFFICE
CERTIFICATE OF CORRECTION

Patent No. 4,843,168  Dated June 27, 1989

Inventor(s) MARK A. DREZDZON; ERIC J. MOORE; and MARK P. KAMINSKY

It is certified that error appears in the above-identified patent and that said Letters Patent is hereby corrected as shown below:

Col. 13, line 27, before "or" add -- , $(W_7O_{24})^{6-}$ --.

Col. 14, line 30, after "removed" add --.--.

Signed and Sealed this

Nineteenth Day of June, 1990

Attest:

HARRY F. MANBECK, JR.

Attesting Officer

Commissioner of Patents and Trademarks